United States Patent [19]

Sugimori et al.

[11] 4,387,039
[45] Jun. 7, 1983

[54] TRANS-4-(TRANS-4'-ALKYLCYCLOHEXYL)-CYCLOHEXANE CARBOXYLIC ACID 4'''-CYANOBIPHENYL ESTER

[75] Inventors: Shigeru Sugimori; Hideo Sato, both of Yokohama, Japan

[73] Assignee: Chisso Corporation, Osaka, Japan

[21] Appl. No.: 278,205

[22] Filed: Jun. 26, 1981

[30] Foreign Application Priority Data

Jun. 9, 1980 [JP] Japan .................... 55-77322

[51] Int. Cl.³ .................... C09K 3/34; G02F 1/13; C07C 61/22; C07C 61/39; C07C 121/48; C07C 121/64

[52] U.S. Cl. .................... 252/299.63; 260/465 D; 260/465 F; 350/350 R; 350/350 S

[58] Field of Search ................ 252/299.63, 299.66, 252/299.65; 260/465 D, 465 R, 465 F; 350/350 R, 350 S

[56] References Cited

U.S. PATENT DOCUMENTS

| 4,013,582 | 3/1977 | Gavrilovic | 252/299.63 |
| 4,029,595 | 6/1977 | Ross et al. | 252/299.63 |
| 4,113,647 | 9/1978 | Coates et al. | 252/299.62 |
| 4,222,887 | 9/1980 | Matsufuji | 252/299.63 |
| 4,227,778 | 10/1980 | Raynes | 252/299.64 |
| 4,228,030 | 10/1980 | Cole, Jr. | 252/299.63 |
| 4,229,315 | 10/1980 | Frause et al. | 252/299.63 |
| 4,253,740 | 3/1981 | Raynes et al. | 252/299.66 |
| 4,261,652 | 4/1981 | Gray et al. | 252/299.62 |
| 4,285,829 | 8/1981 | Eidenschink et al. | 252/299.63 |

FOREIGN PATENT DOCUMENTS

| 19665 | 12/1980 | European Pat. Off. | 252/299.63 |
| 22882 | 1/1981 | European Pat. Off. | 252/299.63 |
| 23728 | 2/1981 | European Pat. Off. | 252/299.63 |
| 23730 | 2/1981 | European Pat. Off. | 252/299.63 |
| 44646 | 1/1982 | European Pat. Off. | 252/299.63 |
| 54-99785 | 8/1979 | Japan | 252/299.63 |
| 2031010 | 4/1980 | United Kingdom | 252/299.66 |

OTHER PUBLICATIONS

Gray, G. W., Mol. Cryst. Liq. Cryst., vol. 53, pp. 3-18 (1981).
Coates, D., et al., Mol. Cryst. Liq. Cryst., vol. 37, pp. 249-262 (1976).
Gray, G. W., et al., Mol. Cryst. Liq. Cryst., vol. 53, pp. 147-166 (1979).
Dewar, M. J. S., et al., J.A.C.S., vol. 92, No. 6, p. 1582-1586 (1976).
The 3rd Symposium on Liquid Crystals, "A Review of Some Liquid Crystal Materials & Their Properties," G. W. Gray, Nov. 1977, pp. 18-19.

Primary Examiner—Teddy S. Gron
Attorney, Agent, or Firm—Wenderoth, Lind & Ponack

[57] ABSTRACT

New ester type nematic liquid crystal compounds as well as a liquid crystal composition containing said compounds are provided, wherein said compounds are trans-4-(trans-4'-alkylcyclohexyl)-cyclohexane carboxylic acid 4'''-cyanobiphenyl esters represented by the general formula of

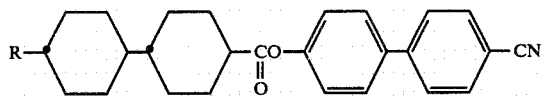

wherein R is straight or branched alkyl group of 1~10 carbon atoms. The compounds are useful as a component of liquid crystal compositions which have a higher N-I temperature since they have a wide mesomorphic temperature range in a higher temperature range.

5 Claims, No Drawings

TRANS-4-(TRANS-4'-ALKYLCYCLOHEXYL)-CYCLOHEXANE CARBOXYLIC ACID 4'''-CYANOBIPHENYL ESTER

BACKGROUND OF THE INVENTION

This invention relates to liquid crystal materials having a wide liquid crystal temperature range and a positive dielectric anisotropy, and to a liquid crystal composition containing them.

Liquid crystal display elements utilize optical anisotropy and dielectric anisotropy, which are characteristics of the liquid crystal material. There are many types of liquid crystal display elements, such as TN (twist nematic) type, DS (dynamic scattering) type, guest-host type and DAP type, etc., in which required characteristics of the liquid crystal materials are different according to their types. In any type, however, it is necessary that the liquid crystal materials are stable to moisture, heat, air and light, etc. and also it is desirable that they show liquid a crystal phase in as wide a temperature range as possible. To date, there has not been found any single compound which can satisfy these conditions, and it is the present status of this art that the compounds obtained by mixing several kinds of the liquid crystal materials are utilized. Recently, a display device operable from low temperature (about $-20°$ C.) to high temperature ($80° \sim 90°$ C.) is particularly required, but it is difficult to satisfy such a requirement by any combination of known compounds.

The compounds of this invention were intended to satisfy such a requirement.

SUMMARY OF THE INVENTION

The present invention resides in trans-4-(trans-4'-alkylcyclohexyl)-cyclohexane carboxylic acid 4'''-cyanobiphenyl esters expressed by the general formula:

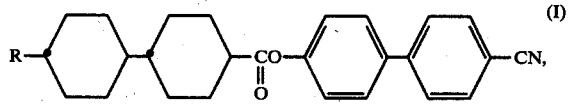

wherein R denotes a straight-chain or branched alkyl group of 1 to 10 carbon atoms.

DESCRIPTION OF THE PREFERRED EMBODIMENTS

The compound of this invention has a wide liquid crystal temperature range in a higher temperature range. For example, trans-4-(trans-4'-propyl cyclohexyl)-cyclohexane carboxylic acid 4'''-cyanobiphenyl has a wide and high nematic temperature range such as from 118° to 460° C. (provided that 460° C. being is an extrapolation value), so that only by adding this compound to a liquid crystal mixture of other compounds in a small amount, the N-I point of the mixture may be raised.

The present invention thus also provides a liquid crystal composition comprising a mixture of compounds at least one of which is a compound of formula (I), for example, a liquid crystal composition comprising a compound of formula (I), 4-alkyl-4'-cyanobiphenyl, trans-4-alkyl-(4'-cyanophenyl)-cyclohexane and trans-4-alkyl-(4''-cyanobiphenyl)-cyclohexane.

The method for preparation of the compounds of this invention is described as follows. Trans-4-(trans-4'-alkylcyclohexyl)-cyclohexane carboxylic acid is first reacted with thionyl chloride to form the acid chloride, which is then reacted with 4'-cyano-4-hydroxy biphenyl in pyridine to give the object compound, trans-4-(trans-4'-alkylcyclohexyl)-cyclohexane carboxylic acid 4'''-cyanobiphenyl ester.

The process is expressed by the following equation.

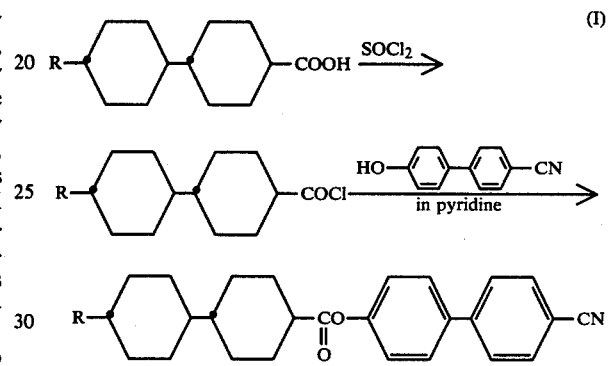

The invention is illustrated in more detail by the following examples.

EXAMPLE 1

Preparation of trans-4-(trans4'-propyl cyclohexyl)-cyclohexane carboxylic acid 4'''-cyanobiphenyl ester.

10 ml of thionyl chloride was added to 0.02 mol (5.0 g) of trans-4-(trans-4'-propyl cyclohexyl)-cyclohexane carboxylic acid and heated. They became homogeneous within about 1 hour, and then they were treated further for about an hour. Thereafter, excess thionyl chloride was removed under reduced pressure to leave trans-4-(trans-4'-propyl cyclohexyl)-cyclohexane carboxylic acid chloride. On the other hand, 3.9 g of 4-4'-cyanophenyl phenol is dissolved in 10 ml of pyridine and the acid chloride was added therein. It was stirred well and left to stand for one night. 200 ml of toluene was added thereto, and the toluene layer was washed with 6N HCl at first, then with 2N aqueous NaOH solution, and finally with water until the wash washing water became neutral. After it was dried with anhydrous sodium sulfate, toluene was removed completely under reduced pressure. The yielded crystals were then recrystallized from acetone to obtain 5.8 g of crystals of trans-4-(trans-4'-propyl cyclohexyl)-cyclohexane carboxylic acid 4'''-cyanobiphenyl ester. Yield: 68%. Its physical properties and elemental analysis are shown in Table 1.

TABLE 1

| Example No. | R in formula (I) | Yield (g) | Yield (%) | C-Sm point | Sm-N point | N-I point | element | anal. value | calc. value |
|---|---|---|---|---|---|---|---|---|---|
| 4 | $C_2H_5$ | 5.5 | 63 | 125 | above 300 | unknown | — | — | — |
| 1 | $C_3H_7$ | 5.8 | 68 | 96 | 118 | (460)* | C | 80.5 | 81.1 |
|   |   |   |   |   |   |   | H | 8.0 | 8.2 |

Phase transition point (°C.)**   Elemental analysis

TABLE 1-continued

| Example No. | R in formula (I) | Yield (g) | Yield (%) | C-Sm point | Sm-N point | N-I point | element | anal. value | calc. value |
|---|---|---|---|---|---|---|---|---|---|
| 5 | C4H9 | 6.0 | 6.5 | 112 | above 300 | unknown | N | 3.1 | 3.3 |
| | | | | | | | C | 80.9 | 81.4 |
| 2 | C5H11 | 6.2 | 68 | 100.8 | above 300 | (430)* | H | 8.4 | 8.6 |
| | | | | | | | N | 3.2 | 3.1 |
| | | | | | | | C | 80.3 | 81.6 |
| 3 | C7H15 | 6.5 | 67 | 93 | above 300 | unknown | H | 8.5 | 8.9 |
| | | | | | | | N | 2.6 | 2.9 |

*extrapolation value from value of mixture with other liquid crystal
**C: solid phase, Sm: smectic phase, N: nematic phase, I: transparent phase (Isomeric phase)

EXAMPLES 2~5

The procedure described in Example 1 was repeated except that 0.02 mol of trans-4-(trans-4'-alkyl cyclohexyl)-cyclohexane carboxylic acids having another alkyl group were used instead of trans-4-(trans-4'-propyl cyclohexyl)-cyclohexane carboxylic acid. Thereby, respective trans-4-(trans-4'-alkyl cyclohexyl)-cyclohexane carboxylic acid 4'''-cyanobiphenyl esters were obtained. Their physical properties and elemental analysis are also shown in Table 1.

EXAMPLE 6

A liquid crystal mixture with the following composition:

| | |
|---|---|
| 4-pentyl-4'-cyanobiphenyl | 40 mol % |
| 4-propoxy-4'-cyanobiphenyl | 10 mol % |
| 4-octyloxy-4'-cyanobiphenyl | 15 mol % |
| trans-4-pentyl-(4'-cyanophenyl)-cyclohexane | 25 mol % |
| trans-4-pentyl-(4''-cyanobiphenyl)-cyclohexane | 10 mol % | may be a practical usable liquid crytal by itself, since it has a nematic temperature range of from −15° C. to 67° C. and the threshold voltage of TN cell with a cell thickness of 10 μm is 1.65 V and the saturated voltage of the cell is 2.30 V.

The mixture obtained by mixing 95 parts of the liquid crystal composition with 5 parts of a compound of this invention, trans-4-(trans-4'-propyl cyclohexyl)-cyclohexane carboxylic acid 4'''-cyanobiphenyl ester, has a much enlarged nematic temperature range of from −15° C. to 81° C. a slightly reduced threshold voltage of 1.62 V and also a slightly reduced saturated voltage of 2.28 V. Thus, practical usage of the liquid crystal obtained is more excellent.

What is claimed is:

1. A trans-4-(trans-4'-alkylcyclohexyl)-cyclohexane carboxylic acid 4'''-cyanobiphenyl ester expressed by the formula

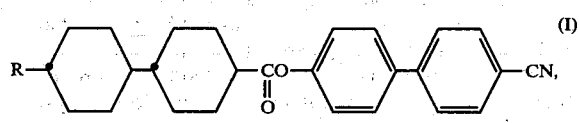

wherein R denotes a straight-chain or branched alkyl group of 1 to 10 carbon atoms.

2. The compound according to claim 1, wherein R is a straight-chain alkyl group of 2 to 7 carbon atoms.

3. The compound according to claim 2, wherein R is C3H7.

4. A liquid crystal composition comprising a mixture of compounds at least one of which is a trans-4-(trans-4'-alkylcyclohexyl)-cyclohexane carboxylic acid 4'''-cyanobiphenyl ester expressed by the formula

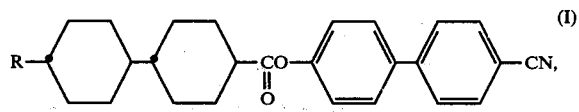

wherein R denotes a straight-chain or branched alkyl group of 1 to 10 carbon atoms.

5. The liquid crystal composition according to claim 4, comprising a compound of formula (I), 4-alkyl-4'-cyanobiphenyl, trans-4-alkyl-(4'-cyanophenyl)-cyclohexane and trans-4-alkyl-(4'-cyanobiphenyl)-cyclohexane.

* * * * *

UNITED STATES PATENT AND TRADEMARK OFFICE
CERTIFICATE OF CORRECTION

PATENT NO. : 4,387,039

DATED : June 7, 1983

INVENTOR(S) : Shigeru Sugimori, and Hideo Sato

It is certified that error appears in the above—identified patent and that said Letters Patent is hereby corrected as shown below:

Column 1, line 21, change "liquid a" to --a liquid--.
Column 2, line 37, change "trans4'" to --trans-4'--;
    line 52, delete "washing".

Signed and Sealed this

Thirteenth Day of September 1983

[SEAL]

Attest:

GERALD J. MOSSINGHOFF

Attesting Officer

Commissioner of Patents and Trademarks